United States Patent [19]
Toge et al.

[11] Patent Number: 5,615,683
[45] Date of Patent: Apr. 1, 1997

[54] OPHTHALMOLOGIC MEASURING APPARATUS

[75] Inventors: Yoshiyuki Toge, Kawasaki; Shinya Tanaka, Tokyo, both of Japan

[73] Assignee: Canon Kabushiki Kaisha, Tokyo, Japan

[21] Appl. No.: 352,506

[22] Filed: Dec. 9, 1994

[30] Foreign Application Priority Data

Dec. 14, 1993 [JP] Japan .................................... 5-343089

[51] Int. Cl.$^6$ ........................................... A61B 5/026
[52] U.S. Cl. ........................................ 128/666; 128/691
[58] Field of Search ........................... 128/653.1, 664, 128/665, 666, 691

[56] References Cited

U.S. PATENT DOCUMENTS

| | | | |
|---|---|---|---|
| 4,346,991 | 8/1982 | Gardner et al. | 128/745 |
| 4,952,050 | 8/1990 | Aizu et al. | 128/691 |
| 4,979,818 | 12/1990 | Kobayashi | 128/691 |
| 5,016,643 | 5/1991 | Applegate et al. | 128/691 |
| 5,058,596 | 10/1991 | Makino et al. | 128/691 |
| 5,090,416 | 2/1992 | Ogino et al. | 128/691 |
| 5,163,437 | 11/1992 | Fuji et al. | |
| 5,394,199 | 2/1995 | Flower | 128/691 |
| 5,549,114 | 8/1996 | Petersen et al. | 128/691 |

FOREIGN PATENT DOCUMENTS

WO9104705  4/1991  WIPO.

*Primary Examiner*—Marvin M. Lateef
*Assistant Examiner*—Brian L. Casler
*Attorney, Agent, or Firm*—Fitzpatrick, Cella, Harper & Scinto

[57] ABSTRACT

An ophthalmologic measuring apparatus has a first projector for applying a first laser beam to a predetermined area of the fundus of an eye to be examined, a first detector for two-dimensionally detecting the reflected light of the first laser beam from the predetermined area, a first measuring device for measuring the blood flow condition in the predetermined area of the fundus of the eye on the basis of a signal obtained by the first detector for detecting the reflected light from the vicinity of a blood vessel in the spot area, a second measuring device for measuring the blood flow velocity in the blood vessel in the spot area on the basis of a signal obtained by the second detector and a calculator for adding the velocity information of each region to the blood flow condition in the predetermined area measured by the first measuring device, on the basis of the result of a measurement by the second measuring device.

14 Claims, 4 Drawing Sheets

5,615,683

OPHTHALMOLOGIC MEASURING APPARATUS

BACKGROUND OF THE INVENTION

1. Field of the Invention

This invention relates to an ophthalmologic measuring apparatus for measuring the condition of the blood flow on the fundus of an eye to be examined.

2. Related Background Art

Such an ophthalmologic measuring apparatus for measuring the condition of a blood flow on the fundus of an eye, as is known from International Laid-Open Patent WO 91/04705, etc., has heretofore been designed such that a laser beam is applied to the fundus of an eye to be examined and the reflected light thereof is photoelectrically detected and the velocity of the blood flow in the retinal tissue on the fundus of the eye to be examined is measured on the basis of this detection signal. This apparatus is constructed such that a speckle pattern, varying moment-by-moment with the movement of red blood cells in the retinal tissue is caught by an image sensor, whereby a speckle signal including the information of the blood flow velocity at each point in time is obtained as a time fluctuation of light intensity, and as a result, the distribution of the blood flow velocity in a predetermined area of the fundus of the eye is measured in terms of a relative value.

In the above-described example of the prior art, however, the blood flow velocity cannot be measured as an absolute value and the above-described apparatus is not always sufficient as an eye fundus blood flow meter.

In addition, the measurements by the methods which are capable of measuring only the relative blood flow value like those described above, depend on the individual 10 eye condition, so that doctor can not compare the result of one patient with another patient.

SUMMARY OF THE INVENTION

It is a first object of the present invention to solve the above-noted problem and to provide an ophthalmologic measuring apparatus which can measure the absolute blood flow velocity.

Other objects of the present invention will become apparent from the following detailed description of an embodiment of the invention.

DESCRIPTION OF THE PREFERRED EMBODIMENT

Figure 1:
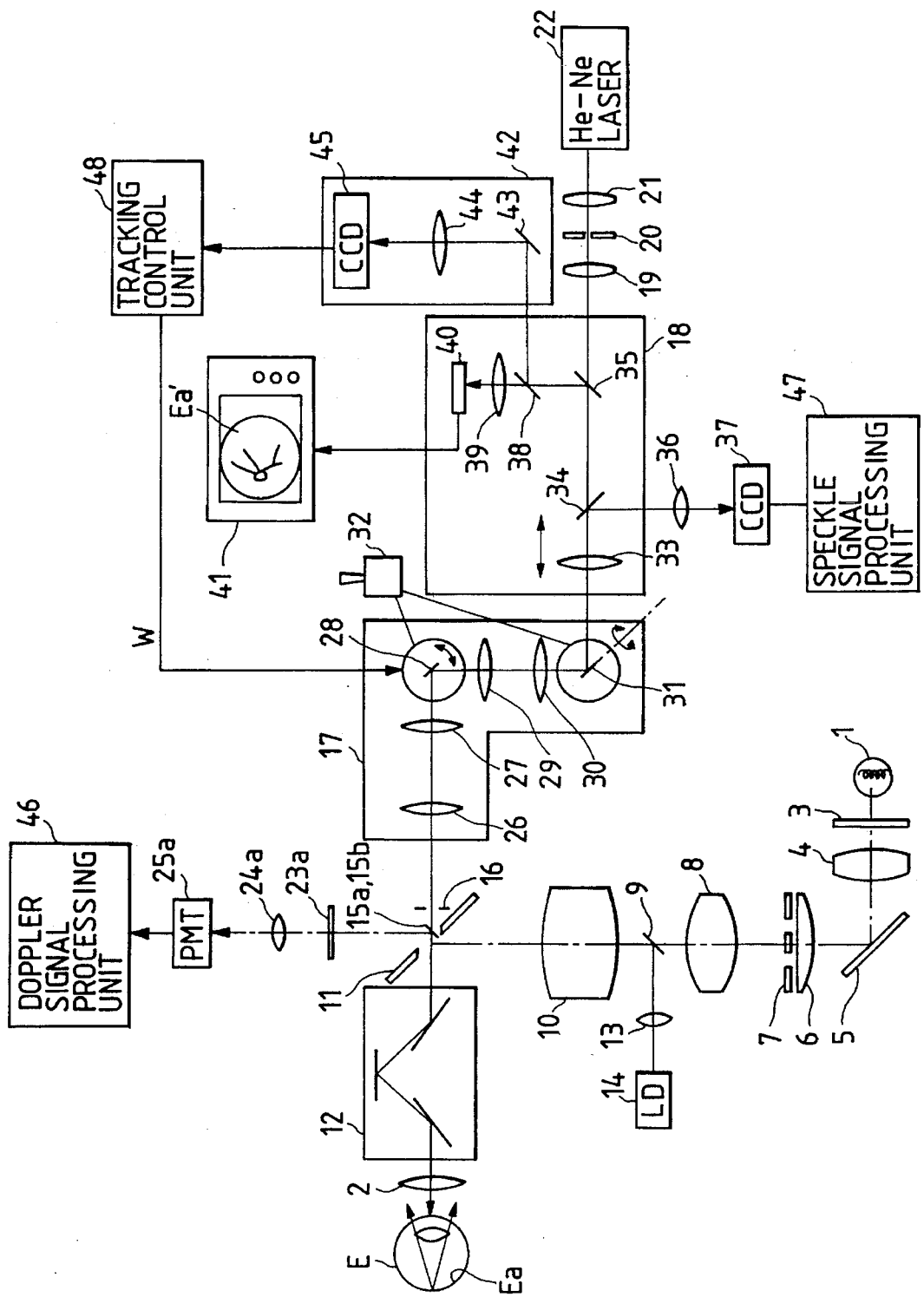
FIG. 1 shows the construction of an embodiment of the present invention.

The invention will hereinafter be described in detail with respect to an embodiment thereof shown in the drawings.

Referring to FIG. 1 which shows the construction of the present embodiment, illustrates a sharp cut filter 3 for intercepting infrared light and transmitting visible light therethrough, a condenser lens 4, a mirror 5, a field lens 6, a ring slit 7 having a ring-shaped opening, a relay lens 8, a dichroic mirror 9 reflecting infrared light including 820 nm and transmitting visible light therethrough, a relay lens 10, an apertured mirror 11 having a hole portion at the center thereof, and an image rotator 12 are arranged on an optical path leading from a light source 1 for observation to an objective lens 2. A collimator lens 13 and a semiconductor laser source 14 emitting a first measuring laser beam which is infrared light of 820 nm are disposed in the direction of incidence of the dichroic mirror 9.

A pair of small mirrors 15a and 15b, an aperture 16, an image stabilizer 17, an observation optical system 18, a lens 19, an aperture 20, a lens 21 and an He-Ne laser source 22 emitting a second measuring laser beam are arranged on an optical path behind the apertured mirror 11. A band-pass filter 23a, lenses 24a, 24b and photomultipliers 25a, 25b are disposed on optical paths in the directions of reflection of respective ones of the pair of small mirrors 15a and 15b. In FIG. 1, in order to avoid duplication, there are shown only the elements on the optical axis of the small mirror 15a of the pair of small mirrors 15a and 15b.

Lenses 26, 27, a galvanometric mirror 28, lenses 29, 30 and a galvanometric mirror 31 are arranged in succession in the image stabilizer 17, and the galvanometric mirrors 28 and 31 are connected to an operating rod 32 provided outside the image stabilizer 17. In this image stabilizer 17, the fundus Ea of an eye E to be examined is made conjugate with the galvanometric mirror 28 by the lenses 26 and 27 and further is made conjugate with the galvanometric mirror 31 by the lenses 29 and 30. The axis of rotation of the galvanometric mirror 28 is set to be perpendicular to the plane of the drawing sheet of FIG. 1, and the axis of rotation of the galvanometric mirror 31 is set in a direction parallel to the plane of the drawing sheet orthogonal to the axis of rotation.

A focusing lens 33 movable on the optical path and dichroic mirrors 34 and 35 reflecting a first laser beam which is infrared light and transmitting visible light therethrough are provided in succession in the observation optical system 18, a lens 36 and a CCD image sensor 37 are disposed in the direction of reflection of the dichroic mirror 34, a television camera 40 is disposed in the direction of reflection of the dichroic mirror 35 through a half mirror 38 and a lens 39, and the output of the television camera 40 is connected to a monochromatic television monitor 41. Also, a blood vessel detecting system 42 is provided in the direction of reflection of the half mirror 38, and a mirror 43, a lens 44 and a one-dimensional CCD sensor 45 with an image intensifier also provided.

The outputs of the photomultipliers 25a and 25b are connected to the input side of a Doppler signal processing unit 46, the output of the CCD image sensor 37 is connected to a speckle signal processing unit 47 and further, the output of the one-dimensional CCD sensor 45 is connected to a tracking control unit 48. Also, the output of the tracking control unit 48 is connected to the galvanometric mirror 28.

In the above-described construction, illuminating light emitted from the light source 1 for observation is imaged on the ring slit 7 through the filter 3, the condenser lens 4, the mirror 5 and the field lens 6. The image on the ring slit 7 is once formed on the apertured mirror 11 by the relay lenses 8 and 10, whereafter it passes through the image rotator 12 and is formed on the pupil of the eye E to be examined by the objective lens 2, and substantially uniformly illuminates the fundus Ea of the eye E to be examined. The field lens 6 acts to direct the beam of light into the eye E to be examined efficiently. On the other hand, the dichroic mirror 9 directs to the fundus Ea of the eye an infrared laser beam as a first measuring laser from the semiconductor laser source 14 having passed through the collimator lens 13.

The illuminating light and the reflected light of the first measuring laser beam from the fundus Ea of the eye again pass through the objective lens 2 and the image rotator 12, pass through the central aperture in the apertured mirror 11 and the aperture 16 and enter the observation optical system 18 via the image stabilizer 17.

The focusing lens 33 and lens 39 of the observation optical system 18 cooperate with each other to form an eye fundus image Ea' on the television camera 40, and the eye fundus image Ea' is displayed on the television monitor 41. An examiner observes this eye fundus image Ea' and effects the alignment of the apparatus and the selection of a region to be measured. On the other hand, the dichroic mirror 34 reflects the first measuring laser beam and directs it to the image sensor 37 conjugate with the fundus Ea of the eye via the lens 36.

The dichroic mirror 35 and the half mirror 38 are respectively for combining and separating a second measuring laser beam emitted from the He-Ne laser source 22 and the optical path of the blood vessel detecting system 42. The blood vessel detecting system 42 forms a beam of light, distributed by the half mirror 38, into a blood vessel image enlarged by the mirror 43 and lens 44 more than on the television camera, on the one-dimensional CCD sensor 45.

The second measuring laser beam emitted from the laser source 22 forms a spot at the position of the aperture 20 conjugate with the fundus Ea of the eye E to be examined by the lens 21 before it is coupled to the observation optical system 18 by the half mirror 38, and that conjugate relationship is adjusted via the lens 19. Accordingly, when the examiner moves the focusing lens 33 on the optical axis thereof to thereby effect the focusing of the fundus Ea of the eye, the image pickup surface of the television camera 40, the image pickup surface of the CCD image sensor 37, the image pickup surface of the one-dimensional CCD sensor 45 and the spot of the second measuring laser beam become conjugate with the fundus Ea of the eye at one time.

The output of the one-dimensional CCD sensor 45 is sent to the tracking control unit 48, which analyzes the blood vessel image and calculates the amount of one-dimensional movement on the one-dimensional CCD sensor 45, thereby generating a drive signal W for the galvanometric mirror 28.

Also, the galvanometric mirrors 28 and 31 have their angles of rotation extraneously changeable by the operating rod 32, and the galvanometric mirror 28 serves to compensate for the fine movement of fixation with respect only to one direction by the drive signal W from the tracking control unit 48. That is, after the examiner has once designated a predetermined blood vessel in the measured area, the galvanometric mirror 28 is driven so that the position of the blood vessel on the one-dimensional CCD sensor 45 may always be constant. At this time, the second measuring laser beam, when it becomes coaxial with the observation optical system 18 by the dichroic mirror 34, reversely follows the optical path thereof and is directed onto the fundus Ea of the eye E to be examined and therefore, that beam of light is always illuminates on a selected blood vessel at the same time.

The second measuring laser beam is reflected by the blood vessel on the fundus Ea of the eye, passes through the objective liens 2 and the image rotator 12 and is received, but part of it is reflected by the pair of small mirrors 15a and 15b overlappingly provided perpendicularly to the plane of the drawing sheet of FIG. 1, rearwardly of the apertured mirror 11, passes through the band-pass filters 23a and 23b and thereafter, is condensed by the lenses 24a and 24b and is received by the photomultipliers 25a and 25b.

Figure 2:
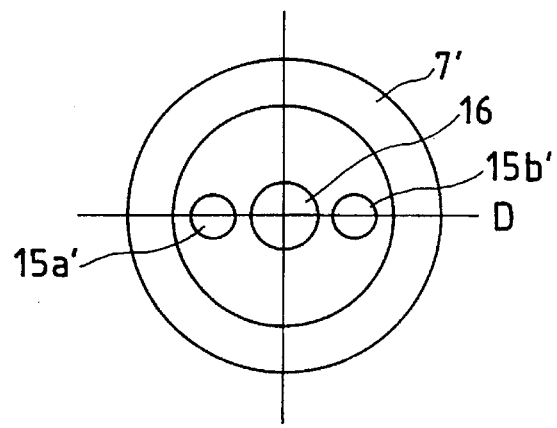
FIG. 2 illustrates the relation between illuminating light and observation light.

Referring now to FIG. 2 which shows the arrangement of the pair of small mirrors 15a, 15b and the illuminating beam of light and the observation beam of light, the reference characters 15a' and 15b' designate the images of the pair of small mirrors 15a and 15b, respectively, at the position of the beam of light for reception, the reference numeral 16' denotes the image of the aperture 16, i.e., the positions of the observation beam of light and the second measuring laser beam, and the reference numeral 7' designates the image of the light transmitting portion of the ring slit 7, i.e., the positions of the illuminating beam of light and the first measuring laser beam.

Figure 3:
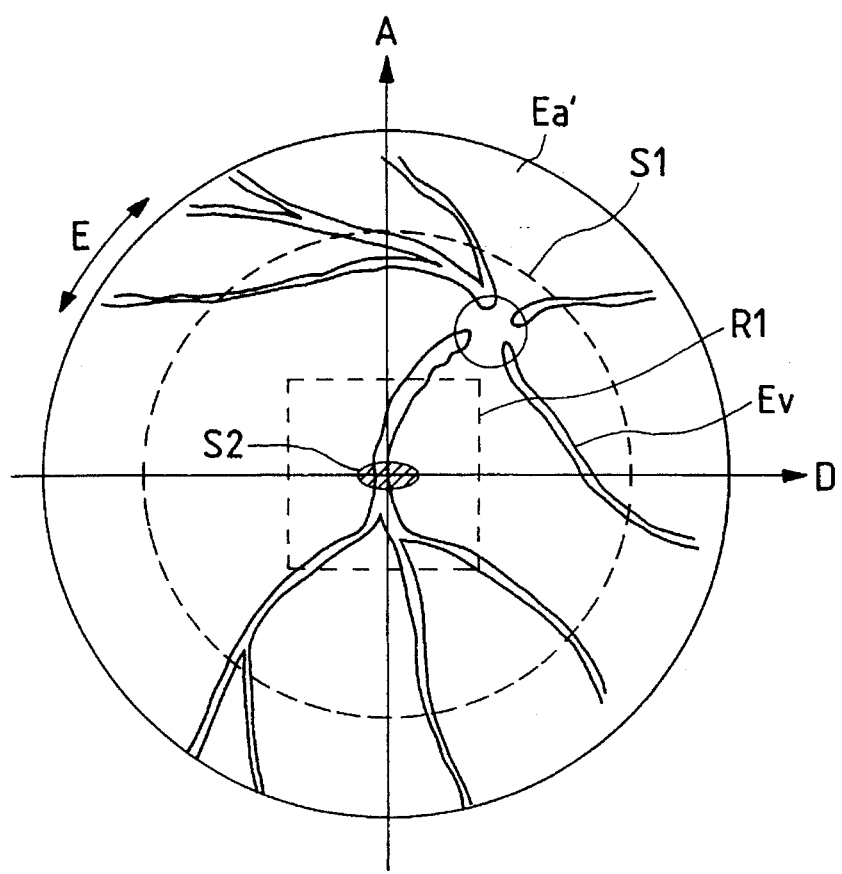
FIG. 3 is an illustration of the image of the fundus of an eye observed.

FIG. 3 shows the condition of the eye fundus image Ea' observed on the television monitor 41, and the other than the image S1 of the first measuring laser beam indicated by a broken line and the image R1 of the light receiving surface of the image sensor 37 which is the measuring area of the speckle signal are observed on the television monitor 41. The coordinate axis A is the line of intersection of a plane formed by the centers of the pair of small mirrors 15a, 15b and the optical axis with the fundus Ea of the eye, and the image S2 of the second measuring laser beam indicates the measuring region of the Doppler signal and is substantially at the center of the image R1.

The examiner first operates the operating rod 32 to thereby make the blood vessel which is substantially at the center of the area to be measured and the spot S2 coincident with each other. At this time, to the examiner, the spot S2 is fixed while remaining positioned at the center relative to the field of view and the eye fundus image Ea' moves and is observed. Thereafter, the image rotator 12 is rotated to thereby rotate the eye fundus image Ea' in the direction of arrow E about the central portion of the field of image, whereby the direction of running of the blood vessel to be measured is made coincident with the direction of arrow A.

When the area to be measured is thus selected, the one-dimensional CCD sensor 45 of the blood vessel detecting system 42 picks up the one-dimensional image in the direction of an axis D orthogonal to the axis A. That is, the galvanometric mirror 28 of the image stabilizer 17 is driven so that during measurement, the position of the blood vessel in the direction D may always be constant.

That portion of the speckle signal from the fundus Ea of the eye by the first measuring laser beam which is within the area R1 is detected by the image sensor 37 and is processed by the speckle signal processing unit 47 as described International Laid-Open Patent WO 91/04705, and the condition of the blood flow velocity in each region of the area R1 is two-dimensionally measured in terms of a relative value. The thus measured two-dimensional blood flow image is displayed as an absolute blood flow amount on the basis of the absolute measurement of the blood flow in the blood vessel at a point obtained by the previously described in method.

Figure 4:
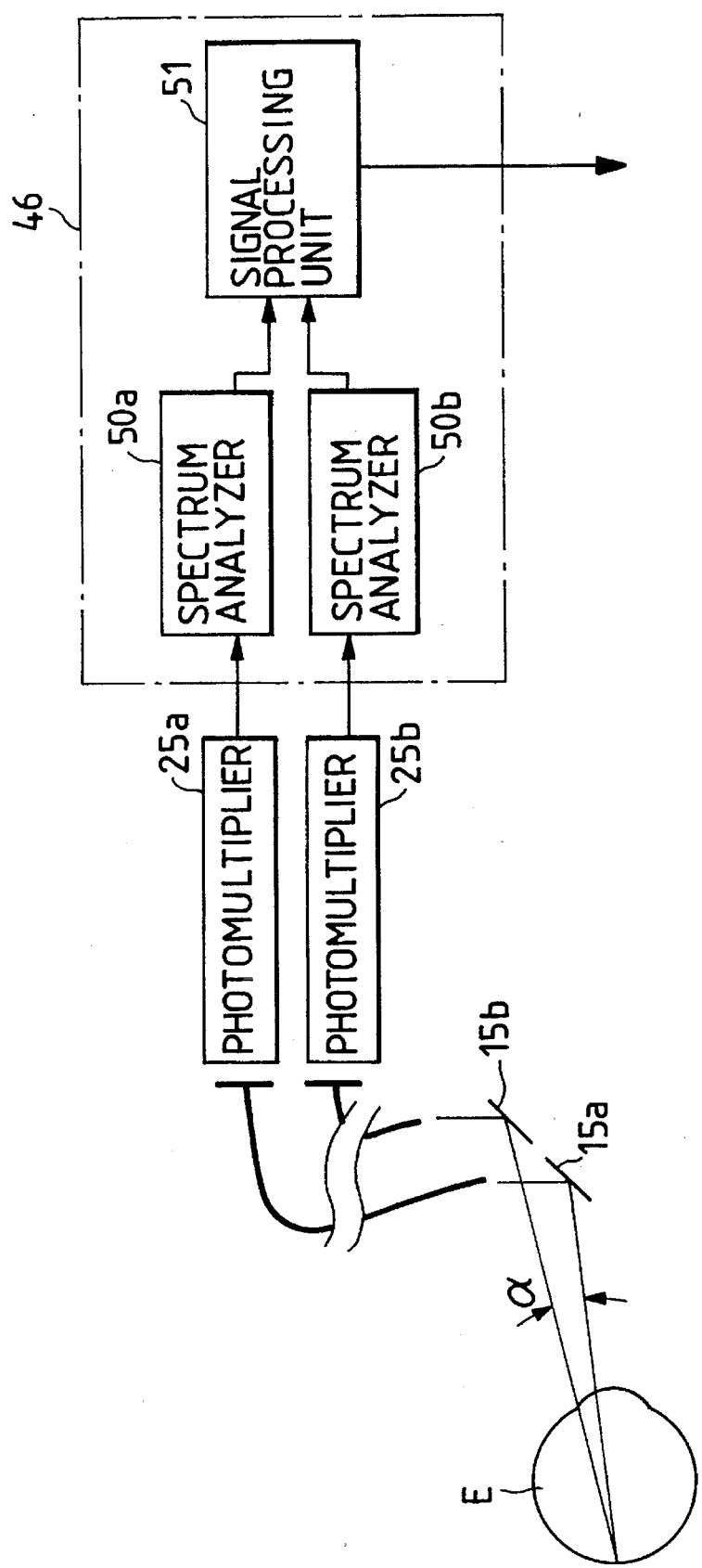
FIG. 4 is a block circuit diagram of a blood flow velocity calculating system.

FIG. 4 is a block circuit diagram of the Doppler signal processing unit 46 which effects the calculation of the blood flow velocity. Signals obtained in the photomultipliers 25a and 25b are Fourier-transformed by spectrum analyzers 50a and 50b and are processed by a signal processing unit 51. In the signal processing unit 51, a maximum velocity Vmax is calculated from the following equation on the basis of two maximum frequencies Δfmax1 and Δfmax2 from the spectrum analyzers 50a and 50b, respectively, whereby the blood flow velocity of the blood vessel in the spot S2 is found.

$$Vmax=(\lambda/n\alpha)\times|\Delta fmax1-\Delta fmax2| \quad (1)$$

where λ is the wavelength of the laser beam, n is the refractive index of the measured region, and α is the angle at which the measured region is subtended from the images 15a' and 15b' shown in FIG. 2.

Figure 5:
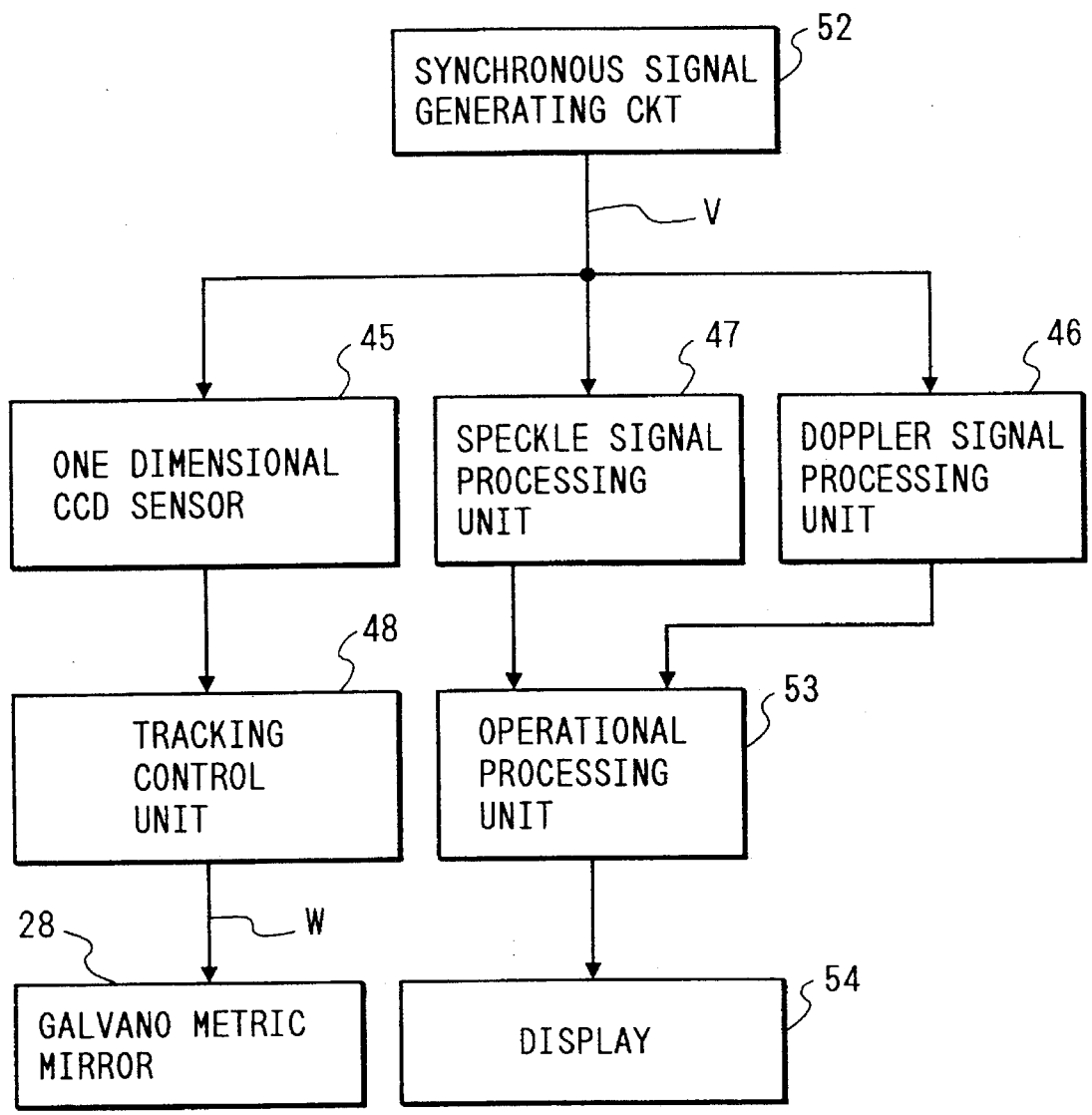
FIG. 5 is a block circuit diagram of a signal processing system.

FIG. 5 is a block circuit diagram of the signal processing circuit. The output side of a synchronous signal generating circuit 52 is connected to the input sides of the one-dimensional CCD sensor 45, the speckle signal processing unit 47 and the Doppler signal processing unit 46, and as previously described, the output of the one-dimensional CCD sensor 45 is connected to the galvanometric mirror 28 via the tracking control unit 48. Also, the outputs of the speckle signal processing unit 47 and the Doppler signal processing unit 46 are both connected to a display unit 54 via an operational processing unit 53.

A synchronous signal V indicative of measurement timing from the synchronous signal generating circuit 52 is supplied to the one-dimensional CCD sensor 45, the speckle signal processing unit 47 and the Doppler signal processing unit 46. In synchronism with this synchronous signal V, the image of the measured region is supplied from the one-dimensional CCD sensor 45 to the tracking control unit 48 and as previously described, the drive signal W for the galvanometric mirror 28 is generated in the tracking control unit 48. Also, signals from the speckle signal processing unit 47 and the Doppler signal processing unit 46 are processed by the operational processing unit 53, and the blood flow condition which is the result thereof is displayed as an absolute value on the display unit 54 such as a display or a plotter.

The operational processing unit 53 first discriminates the regions at which the blood vessels exist from a two-dimensional map by the utilization of the fact that the blood flow in the blood vessel is very fast relative to the other regions, and then the velocity in that discriminated blood vessel is converted on the basis of the absolute blood flow velocity in the region found by the Doppler signal processing unit 46 and is displayed on the display unit 54. Likewise, the blood flows in the other regions are actually not blood flows in one direction, but they are displayed as values converted into blood flows in the blood vessels, for comparison between blood flows of different patients.

On the basis of the above-described information, it is possible to effect accurate measurement of the blood flow condition useful for the medical diagnosis of arteriosclerosis, diabetes, etc.

As described above, the ophthalmologic measuring apparatus of the above-described embodiment can calculate the blood flow velocity in a predetermined blood vessel and as a result, can find the blood flow velocity in a blood vessel in a measured area in terms of an absolute value and therefore is very effective for effecting the analysis of the flow velocity and flow rate with regard to a blood vessel branching off into a number of blood vessels and thus, it becomes possible to accurately grasp the blood flow condition of these branch blood vessels, and the region except retinal vessels, of which the absolute value is useful to compare the blood flows of different patients with each other.

It goes without saying that the invention can be applied as two dimensional measuring method to all methods capable of obtaining relative blood flow information, without limiting the embodiment.

What is claimed is:

1. An opthalmologic measuring apparatus comprising:

first projection means for applying a first laser beam to a predetermined area of a fundus of an eye to be examined;

first detecting means for two-dimensionally detecting reflected light of said first laser beam from said predetermined area;

first measuring means for measuring a blood flow condition two-dimensionally in said predetermined area of the fundus of the eye on the basis of a signal obtained by said first detecting means;

second projection means for applying a second laser beam to a spot area including at least one blood vessel in said predetermined area of the fundus of the eye;

second detecting means for detecting reflected light from said spot area;

second measuring means for measuring a blood flow velocity in a blood vessel in said spot area on the basis of a signal obtained by said second detecting means; and calculating means for adding velocity information of each region of said predetermined area to the blood flow condition in said predetermined area measured by said first measuring means, on the basis of a result of a measurement by said second measuring means.

2. The apparatus of claim 1, further comprising display means for displaying a blood flow map in said predetermined area measured by said first measuring means.

3. The apparatus of claim 1, further comprising display means for displaying velocity information of each region of said predetermined area calculated by said calculating means.

4. The apparatus of claim 1, wherein said first measuring means processes a speckle signal obtained from said first detecting means, and two-dimensionally measures a condition of the blood flow velocity in each region of said predetermined area in terms of a relative value.

5. The apparatus of claim 4, wherein said calculating means converts a relative value indicative of the blood flow condition of each region of said predetermined area into an absolute blood flow velocity on the basis of the blood flow velocity in the blood vessel in said spot area obtained by said second measuring means.

6. The apparatus of claim 1, wherein said second measuring means processes a Doppler signal obtained from said second detecting means and measures the blood flow velocity in the blood vessel in said spot area.

7. The apparatus of claim 6, further comprising tracking means for roughly fixing said first laser beam on said spot area.

8. The apparatus of claim 1, wherein said spot area exists in said predetermined area.

9. The apparatus of claim 1, wherein said calculating means discriminates blood vessels in said predetermined area on the basis of the measurement of said first measuring means and calculates absolute velocity information of each region of said predetermined area of the discriminated blood vessels.

10. An eye fundus blood flow measuring apparatus comprising:

a first laser source generating a first laser beam;

a first projection optical system for applying the first laser beam to a predetermined area of a fundus of an eye to be examined;

a detecting system for two-dimensionally detecting reflected light of said first laser beam from said predetermined area;

a first signal processing unit for measuring a blood flow condition two-dimensionally in said predetermined area of the fundus of the eye on the basis of a signal obtained by said detecting system;

a second laser source generating a second laser beam;

a second projection optical system for applying the second laser beam to a spot area including at least one blood vessel in said predetermined area of the fundus of the eye;

a photosensor for detecting reflected light from said spot area;

a second signal processing unit for measuring a blood flow velocity in a blood vessel in said spot area on the basis of a Doppler signal obtained by said photosensor; and an operational processing unit for adding velocity information of each region of said predetermined area to the blood flow condition of said predetermined area measured by said first signal processing unit, on the basis of a result of a measurement by said second signal processing unit.

11. The apparatus of claim 10, further comprising a display unit for displaying a blood flow map in said predetermined area measured by said first signal processing unit.

12. The apparatus of claim 10, further comprising a display unit for displaying velocity information of each region of said predetermined area calculated by said operational processing unit.

13. The apparatus of claim 10, wherein said operational processing unit discriminates blood vessels in said predetermined area on the basis of the measurement of said first signal processing unit and calculates absolute velocity information of each region of said predetermined area of the discriminated blood vessels.

14. The apparatus comprising:

first laser source generating a first laser beam;

a first projection optical system for applying the first laser beam to a predetermined area of a fundus of an eye to be examined;

a detecting system for two-dimensionally detecting reflected light of said first laser beam from said predetermined area;

a first signal processing unit for measuring a blood flow condition two-dimensionally in said predetermined area of the fundus of the eye on the basis of a signal obtained by said detecting system;

wherein said first signal processing unit measures a relative value indicative of a blood flow condition of each region of said predetermined area, a second laser source generating a second laser beam;

a second projection optical system for applying the second laser beam to a spot area including at least one blood vessel in said predetermined area of the fundus of the eye;

a photosensor for detecting reflected light from said spot area;

a second signal processing unit for measuring a blood flow velocity in the blood vessel in said spot area on the basis of a Doppler signal obtained by said photosensor; and an operational processing unit for adding velocity information of each region of said predetermined area to the blood flow condition of said predetermined area measured by said first signal processing unit, on the basis of a result of a measurement by said second signal processing unit herein said operational processing unit converts the relative value indicative of the blood flow condition of each region of said predetermined area into an absolute blood flow velocity, on the basis of the blood flow velocity in the blood vessel in said spot area obtained by said second signal processing unit.

* * * * *

UNITED STATES PATENT AND TRADEMARK OFFICE
CERTIFICATE OF CORRECTION

PATENT NO. : 5,615,683
DATED : April 1, 1997
INVENTOR(S) : TOGE, et al.

It is certified that error appears in the above-indentified patent and that said Letters Patent is hereby corrected as shown below:

Column 1

Line 35, "10" should be deleted.

Column 2

Line 51, "intensifier" should read --intensifier are--.

Column 3

Line 62, "is" should be deleted.

Line 63, "on" should be deleted.

UNITED STATES PATENT AND TRADEMARK OFFICE
CERTIFICATE OF CORRECTION

PATENT NO. : 5,615,683
DATED : April 1, 1997
INVENTOR(S) : TOGE, et al.

It is certified that error appears in the above-indentified patent and that said Letters Patent is hereby corrected as shown below:

Column 4

Line 54, "described" should read --described in--.

Line 60, "in" should be deleted.

Column 8

Line 34, "herein" should read --wherein--.

Signed and Sealed this

Fourteenth Day of October, 1997

*Attest:*

BRUCE LEHMAN

*Attesting Officer*    Commissioner of Patents and Trademarks